United States Patent [19]

Maffei et al.

[11] Patent Number: 4,467,794
[45] Date of Patent: Aug. 28, 1984

[54] INTRAMEDULARY BONE-SETTING ASSEMBLY

[76] Inventors: Ernest Maffei, 1681 James St., Syracuse, N.Y. 13203; David W. Patch, Rte. #2, Clarkesville, Ga. 30523

[21] Appl. No.: 346,580

[22] Filed: Feb. 8, 1982

[51] Int. Cl.³ .............................................. A61F 5/04
[52] U.S. Cl. ............................ 128/92 BC; 128/92 B; 128/92 R; 403/47
[58] Field of Search ............ 128/92 B, 92 BC, 92 BB, 128/92 BA, 92 E, 92 D; 403/43, 44, 45, 47

[56] References Cited

U.S. PATENT DOCUMENTS

| 3,744,488 | 7/1973 | Cox | 128/92 BC |
| 4,016,874 | 4/1977 | Maffei et al. | 128/92 BC |
| 4,187,841 | 2/1980 | Knutson | 128/92 E |
| 4,262,665 | 4/1981 | Roalstad et al. | 128/92 BC |

FOREIGN PATENT DOCUMENTS 2823954  12/1979  Fed. Rep. of Germany .... 128/92 B

*Primary Examiner*—Richard J. Apley
*Assistant Examiner*—David J. Isabella
*Attorney, Agent, or Firm*—Bruns & Wall

[57] ABSTRACT

A bone-setting assembly essentially comprised of a pair of tubular members adapted to be inserted in the intramedullary passages of the respective parts of a broken bone, and a central connecting and aligning pin that is arranged to be slidably received in the interior passages of the tubular members. The tubular members are driven into position in the bone passages and a portion of the exterior surface of each member is roughened to firmly fix the member in the bone. The interior passages of the tubular members are preferably square in cross section and the central pin has a conforming square cross section so that there can be no relative rotation between the tubular members and thus between the parts of the broken bone. The central pin is threaded over approximately half of its length and a nut is threaded on this portion of the pin. After the tubular members have been positioned in the respective parts of the broken bone, the central pin is inserted in one of the members with only the end of its threaded portion extending outwardly from the tubular member and having the nut threaded thereon. The central pin is then advanced longitudinally into the other tubular member by turning the nut and this advance continues until the nut reaches the end of the threaded portion of the pin at which time approximately half of the pin will be positioned in each tubular member.

4 Claims, 5 Drawing Figures

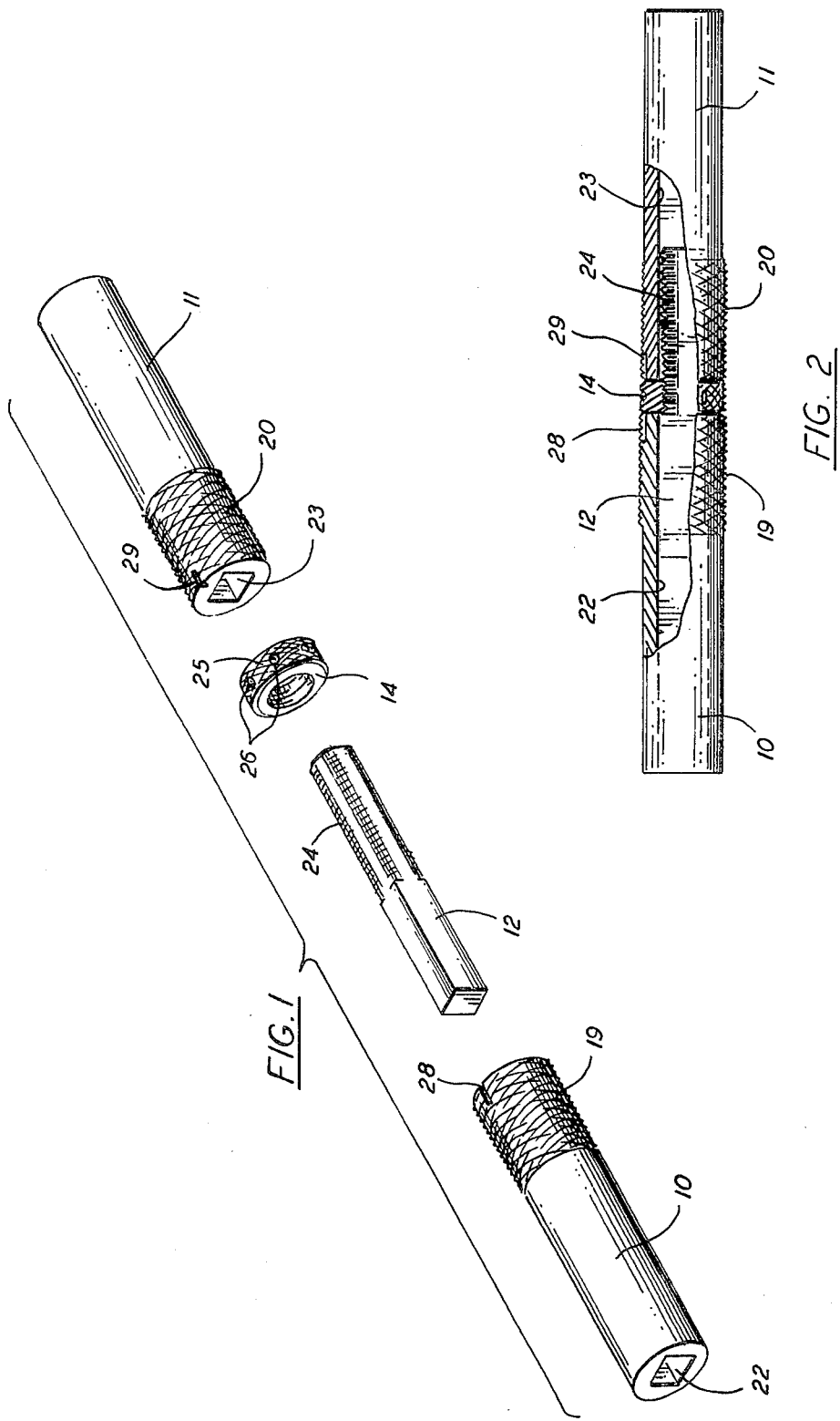

INTRAMEDULARY BONE-SETTING ASSEMBLY

BACKGROUND OF THE INVENTION

This invention relates generally to surgical devices, and has particular reference to an improved intramedullary bone-setting assembly. The bone setting assembly of the invention is adapted to be inserted in the intramedullary passage of the two parts of an elongated broken bone, such as an arm or leg bone. The insertion is made through an incision in the limb at the break, and the purpose of the assembly is to align the broken parts of the bone and to prevent rotation or torsion of one part with respect to the other.

Prior art bone-setting devices either have exterior plate members secured to the bone parts by pins or screws which injure the flesh and muscle surrounding the bone or have similar transversely extending fastening devices through the bone which weaken the hard outer layer of the bone. Other devices must be inserted from one end of the bone and then removed after the fracture has healed. Still other devices keep the parts of the bone on either side of the fracture in alignment but do not prevent rotation of one bone part about the bone axis with respect to the other part. Such devices require immobilizing casts or other restraining means which must be worn for a considerable length of time to prevent torsional movement of the bone parts.

The closest prior art known to the applicants is their own U.S. Pat. No. 4,016,874 granted Apr. 12, 1977 for a Three-Part Intramedullary Bone-Setting Pin. The device disclosed by this patent comprises a pair of tubular parts that are threaded into the respective parts of a broken bone and a central connecting and aligning pin that, in finally assembled form, is positioned in the tubular parts with approximately half its length in each. The pin and interior passages of the tubular parts are preferably square in cross section so that relative rotation between the parts is prevented. A disadvantage of this prior device is the need for threading the tubular parts into the respective bone parts.

Other prior art developed in searches made subsequent to the grant of U.S, Pat. No. 4,016,874 is disclosed in U.S. Pat. Nos. 3,986,504; 4,024,531; 4,091,806; 4,187,841; 4,227,518; 4,237,875 and 4,275,717.

SUMMARY OF THE INVENTION

The bone-setting assembly of the present invention is essentially comprised of a pair of tubular members adapted to be inserted in the intramedullary passages of the respective parts of a broken bone, and a central connecting and aligning pin that is arranged to be slidably received in the interior passages of the tubular members. The tubular members are adapted to be driven into position in the bone passages and a portion of the exterior surface of each member is knurled or otherwise roughened to firmly fix the member in the bone. The interior passages of the tubular members are preferably square in cross section and the central pin has a conforming square cross section so that there can be no relative rotation between the tubular members and thus between the parts of the broken bone.

The central pin is threaded over approximately half of its length and a nut is threaded on this portion of the pin. After the tubular members have been positioned in the respective parts of the broken bone, the central pin is inserted in one of the members with only the end of its threaded portion extending outwardly from the tubular member and having the nut threaded thereon. Thereafter, the retracting apparatus that is holding the parts of the broken bone apart is adjusted to bring the bone parts into alignment and closer together. The central pin is then advanced longitudinally into the other tubular member by turning the nut and this advance will continue until the nut reaches the end of the threaded portion of the pin at which time approximately half of the pin will be positioned in each tubular member. This means for longitudinally moving the pin and properly locating it is easier and somewhat more positive than the means employed for the same purpose in the applicant's U.S. Pat. No. 4,016,874.

BRIEF DESCRIPTION OF THE DRAWINGS

FIG. 1 is an enlarged, exploded perspective view of a bone-setting assembly embodying the invention;

FIG. 2 is an enlarged side elevation of the assembly with a portion broken away to show details of the construction;

DESCRIPTION OF THE PREFERRED EMBODIMENT

Figure 3:
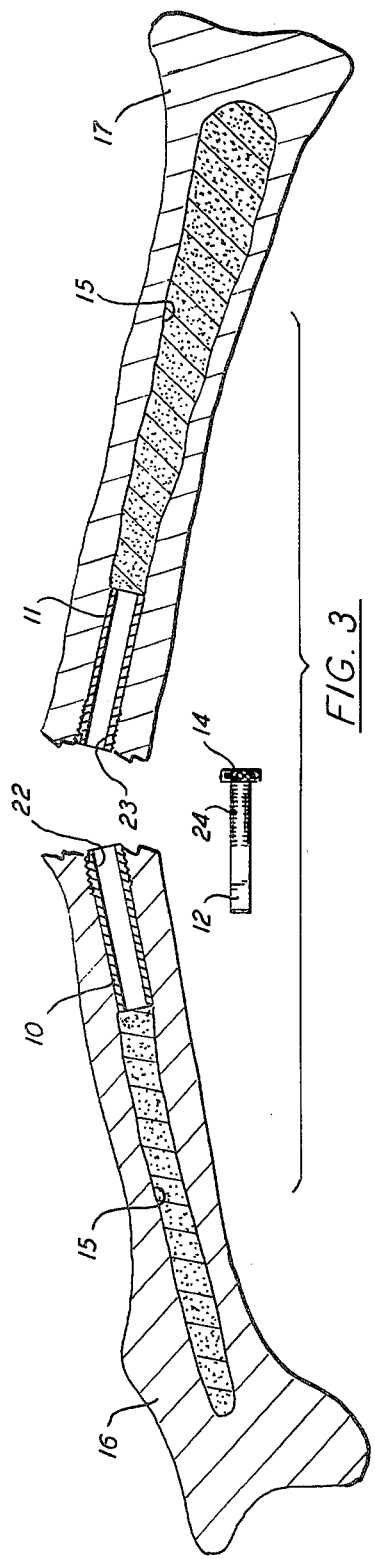
FIG. 3 is a diagrammatic longitudinal sectional view showing the two parts of a broken bone with the tubular members of the bone-setting assembly positioned therein and the central pin ready to insert in one of the members.

Having reference now to the drawings, and with particular reference to FIGS. 1 and 2, the bone-setting assembly comprises a pair of tubular members 10 and 11, a central connecting and aligning pin 12 and a nut 14 adapted to be threaded on the pin for a purpose to be described hereinafter. The tubular members are adapted to be fixedly secured in the intramedullary passage 15, FIG. 3, of the two parts 16 and 17 of a broken bone and to this end a portion of each member is knurled, scored or otherwise roughened adjacent one end as indicated at 19 and 20. The diameter of the members 10 and 11 is slightly greater where they are roughened so that these portions of the members will project out slightly and grip the hard part of the bone surrounding the intramedullary passage.

The connecting and aligning pin 12 is adapted to be received with a sliding fit in the interior passages 22 and 23 of the tubular members 10,11. Since there can be no relative rotation between the members 10 and 11 and thus between the parts of the broken bone, the interior passages 22,23 and the pin are formed with conforming polygonal cross sections, a square cross section as shown being preferred. Alternatively, a key arrangement (not shown) can be employed to prevent relative rotation.

As best shown in FIG. 1, the pin 12 is threaded over approximately one-half its length as indicated at 24, the square cross section of the pin resulting in alternate threaded and flat areas whereby the functionality of the pin's square cross section is retained throughout its length. The nut 14 is adapted to engage the threaded portion 24 of the pin for moving the pin longitudinally relative to the tubular members 10 and 11 as will be described in more detail hereinafter. To facilitate turning the nut, it is provided with a knurled surface as shown at 25 and, in addition, it may be provided with a series of circumferentially spaced indentations 26.

It will be understood that for the pin 12 to connect the members 10 and 11, the square passages 22,23 of the members must be in close radial alignment with one another. To this end, suitable alignment means for the members are provided such as the notches 28 and 29, FIG. 1.

Figure 4:
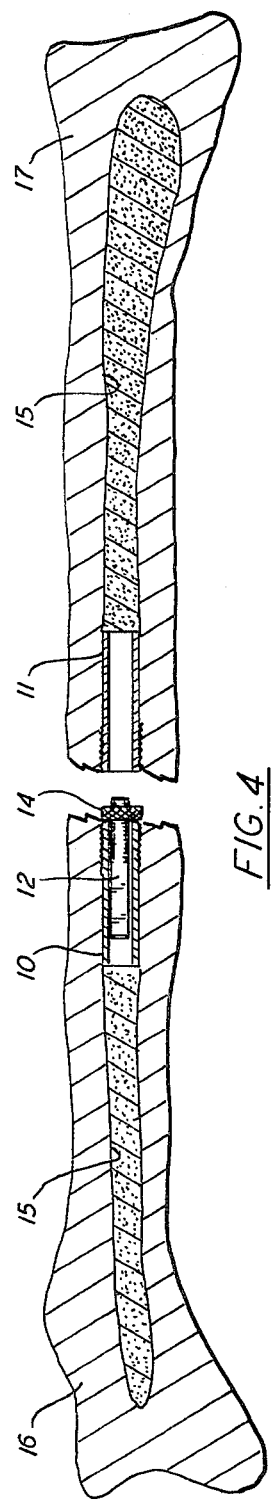
FIG. 4 is a view corresponding to FIG. 3 after the central pin has been inserted in one of the tubular members and the parts of the broken bone have been brought into substantial alignment.
Figure 5:
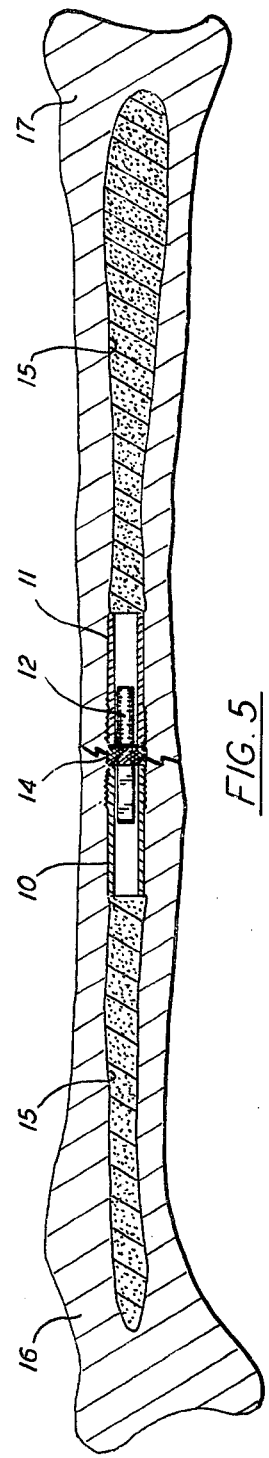
FIG. 5 is a view corresponding to FIG. 4 but with the parts of the bone no longer retracted and the device of the invention in its finally assembled form in the intramedullary passage of the bone.

FIGS. 3-5 diagrammatically illustrate how the bone-setting assembly just described is inserted in the broken bone. In FIG. 3, the parts 16 and 17 of the broken bone have been retracted from one another by conventional surgical retractor means (not shown) and angularly displaced to permit access to the intramedullary passage in each part. The bone parts are drilled to permit the tubular members 10,11 to be inserted therein. Insertion of the members is accomplished by tapping them into position as by a small hammer whereby the knurled portions 19 and 20 of the members rigidly engage the cortex or hard part of the bone surrounding the intramedullary passage.

After the members 10,11 have been fixed in position in the respective parts 16,17 of the bone, the pin 12 is inserted in the passage of one of the members, this being the left hand member 10 in the illustrated example, FIG. 4. Before inserting the pin, the nut 14 is threaded onto the outer end of its threaded portion 24 so that just the nut and outer threaded end of the pin project out from the tubular member passage as indicated in FIG. 4. This is done while the parts of the bone are still retracted and angularly displaced as shown in FIG. 3.

Following the positioning of the pin 12 and nut 14 in one of the tubular members, the retractor means is adjusted to bring the parts 16 and 17 of the bone into alignment and closer together as shown in FIG. 4. The nut is then turned to cause the pin to move longitudinally to the right whereby it advances into the right hand tubular member 11. The longitudinal movement of the pin is caused by the conforming square cross sections of the pin and tubular members whereby relative rotation between these parts is not permitted.

The nut 14 can be turned by a suitable instrument that frictionally engages the knurled surface of the nut or by a pick type instrument that coacts with the indentations 26 in the nut. The nut is turned until it reaches the inner end of the threaded portion of the pin at which point it can be turned no more and the pin will be positioned with approximately half of its length in each tubular member as indicated in FIGS. 2 and 5. This construction provides a simple and very positive means for locating the pin 12 in the final assembly.

After the pin has been advanced as far as it will go into the tubular member 11, the retractor means is removed altogether and the ends of the bone parts 16,17 are brought close together by the natural muscle and sinew contractions in the affected limb, see FIG. 5. This action is permitted due to the fact that the pin 12 is slidable in the tubular members which is desirable whereas any relative rotation or torsion between the members is definitely not wanted as it would inhibit the healing process.

The tubular members 10 and 11 of the bone-setting assembly are interchangeable and either can be a right or left member. This is an advantage over the construction disclosed in applicants' U.S. Pat. No. 4,016,874 wherein the corresponding members are not interchangeable due to the necessity for left and right hand threads. It will be understood that the members 10,11 can be made with different diameters and lengths so as to adapt them for bones of different sizes, breaks near the end of a bone, etc. Also, in a particular bone-setting assembly, the tubular members 10,11 may not be of equal length. For other advantages of, and considerations in regard to, intramedullary bone-setting assemblies or devices, reference is made to U.S. Pat. No. 4,016,874 which has a fuller discussion thereof.

From the foregoing description it will be apparent that the present invention provides an improved and very advantageous intramedullary bone-setting assembly. As will be understood by those familiar with the art, the invention may be embodied in other specific forms without departing from the spirit or essential characteristics thereof.

We claim:

1. A bone-setting assembly for aligning and mutually non-rotatably securing together two portions of a fractured bone, comprising a pair of tubular members adapted to be inserted into the intramedullary bone passages of the respective bone portions at the point of fracture, each tubular member having a substantially cylindrical exterior surface and an interior passage that is polygonal in cross section, means consisting of a knurled or scored surface at one end of each tubular member to secure it in fixed relation in its respective bone portion, the other end of each member having a smooth cylindrical surface, a central connecting and aligning pin adapted to be received with a sliding fit in the hollow interior passages of the tubular members, the pin having a polygonal cross section conforming to that of the tubular member passages whereby relative rotation between the pin and members is prevented, the pin being threaded over approximately one-half of its length while retaining its polygonal cross section in the threaded portion, and a nut threaded on the pin and being operable to move the pin longitudinally in the tubular member passages so that it can be positioned with approximately one-half of its length in each tubular member.

2. A bone-setting assembly as defined in claim 1 wherein the tubular member passages and the pin have conforming square cross sections.

3. A bone-setting assembly as defined in claim 1 wherein the pin includes shoulder means at the inner end of its threaded portion, the shoulder means serving as a stop for the nut.

4. A bone-setting assembly as defined in claim 1 together with means on the respective tubular members for enabling them to be radially aligned with each other when they are inserted into the bone passages.

* * * * *